(12) United States Patent
Preece

(10) Patent No.: US 6,825,487 B2
(45) Date of Patent: Nov. 30, 2004

(54) METHOD FOR ISOLATION OF WAFER SUPPORT-RELATED CRYSTAL DEFECTS

(75) Inventor: Brazel G. Preece, Vancouver, WA (US)

(73) Assignee: Seh America, Inc., Vancouver, WA (US)

( * ) Notice: Subject to any disclaimer, the term of this patent is extended or adjusted under 35 U.S.C. 154(b) by 132 days.

(21) Appl. No.: 10/207,028

(22) Filed: Jul. 30, 2002

(65) Prior Publication Data

US 2004/0021097 A1 Feb. 5, 2004

(51) Int. Cl.$^7$ ............................................. G01N 21/86
(52) U.S. Cl. .............................. 250/559.4; 250/559.45; 356/237.4
(58) Field of Search ......................... 250/559.4, 559.45, 250/559.43, 559.22; 356/237.1, 239.7, 237.4, 237.5; 438/7, 15, 16

(56) References Cited

U.S. PATENT DOCUMENTS

| | | | |
|---|---|---|---|
| 6,245,152 B1 | 6/2001 | Imai et al. | |
| 6,362,487 B1 | 3/2002 | Ehlert et al. | |
| 6,528,333 B1 * | 3/2003 | Jun et al. | 438/16 |

OTHER PUBLICATIONS

TePla Brochure, *The Power of Laser*, Date and Author: Unknown, no date.
H.D. Geiler, "Cracks Found by SIRD–Imaging in Silicon Wafers", *JenaWave Engineering & Consulting* vol. 1, No. 1, (Jun. 1999).
H.D. Geiler, "Pin–Mark Hunting after RTP", *JenaWave Engineering & Consulting* vol. 1, No. 2, (Jun. 1999).
H.D. Geiler, "Slipline Detection after Epitaxy by SIRD", *JenaWave Engineering & Consulting* vol. 1, No. 3, (Jun. 1999).
H.D. Geiler, "6–GaAs wafers controlled by SIRD", *JenaWave Engineering & Consulting* vol. 1, No. 4, (Jun. 1999).
H. Karge, "Visualization of Elastic Stress in 300mm Wafers fixed in a POD", *JenaWave Engineering & Consulting* vol. 1, No. 5, (Jun. 1999).
H.D. Geiler, "Danger Potential of "Crow Feet" evaluated by SIRD", *TePla AG*, vol. 2, No. 1, (Dec. 1999).
H.D. Geiler et al. "Subsurface damage—an up–stream problem", *TePla AG*, vol. 2, No. 2, (Dec. 1999).
Matthias Wagner et al., "Fast and Non–Destructive Detection of Crystal Defects in Wafers by Imaging of Local Stress", *SEMI TechnologySymposium*, Session 7, pp. 1–8, (1999), month unknown.
H.D. Geiler et al., "Photoelastic Imaging of Process Induced Defects in 300mm–Silicon Wafers", *MRS Meeting Session S*, pp. 1–5, (Nov. 1999).

* cited by examiner

*Primary Examiner*—Que T. Le
(74) *Attorney, Agent, or Firm*—Oliff & Berridge, PLC

(57) ABSTRACT

A method of measurement of wafers to isolate wafer support-related defects involves Scanning Infrared Depolarization (SIRD) measurement of multiple processed wafers, each oriented differently on the wafer support, to obtain and characterize depolarization stress defects. The method mounts first and second wafers in first and second orientations and performs a SIRD scan of each. The results are correlated to isolate orientation dependent defects from non-orientation dependent defects. Orientation dependent defects are characterized as wafer support-related defects. Analysis of such wafer support-related defects may then be used to identify and correct the corresponding wafer support defect.

17 Claims, 12 Drawing Sheets

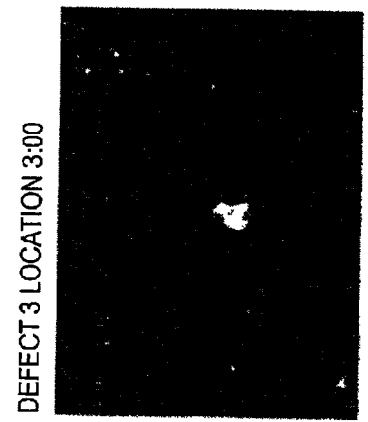
FIG. 8A — DEFECT 1 LOCATION 5:00
FIG. 8B — DEFECT 2 LOCATION 4:00
FIG. 8D — BEFORE BEVEL POLISH
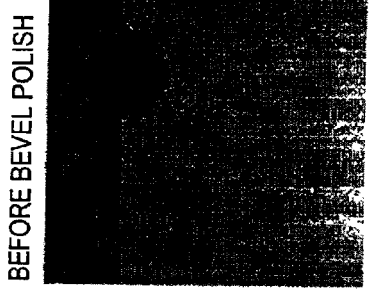
FIG. 8E — BEFORE BEVEL POLISH
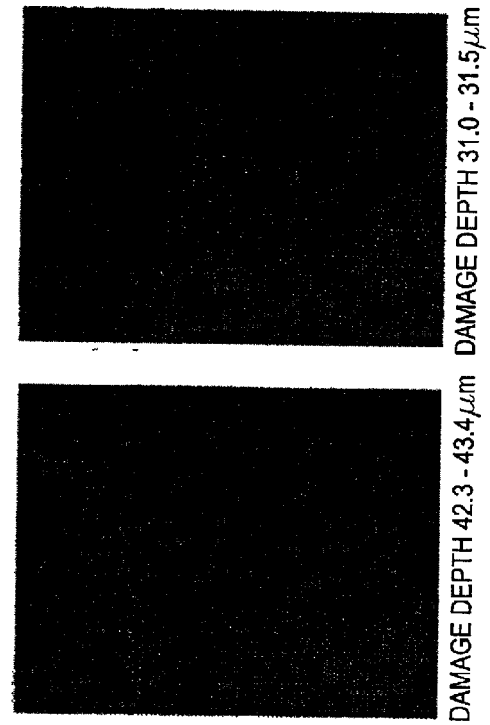
FIG. 8C — DEFECT 3 LOCATION 3:00
FIG. 8F — DAMAGE DEPTH 42.3 – 43.4 μm
FIG. 8G — DAMAGE DEPTH 31.0 – 31.5 μm

SLOT 8 (20) NOTCH - 180° LASERMARK SIDE UP

SLOT 6 (18) NOTCH - 270° LASERMARK SIDE ON SUSCEPTOR

SLOT 12 (24) NOTCH -0° LASERMARK SIDE UP

SLOT 10 (22) NOTCH -90° LASERMARK SIDE ON SUSCEPTOR

METHOD FOR ISOLATION OF WAFER SUPPORT-RELATED CRYSTAL DEFECTS

BACKGROUND OF THE INVENTION

1. Field of Invention

The invention relates to methods for detection and characterization of semiconductor material defects. In particular, methods for isolation of semiconductor wafer support-related defects are provided using scanning infrared depolarization.

2. Description of Related Art

Semiconductor materials, such as silicon or GaAs, are used to make components, such as integrated circuits. Typically, these are formed from a moncrystalline semiconductor material in the shape of a wafer sliced from a silicon crystal ingot. This wafer is then subjected to several processing steps to form a final product. However, in order to be suitable for further upstream processing, the semiconductor material must be entirely or substantially free of crystal defects. Such defects may include, for example, dislocations, cracks, microflaws, sliplines, scratches, foreign particulate matter, and the like. These defects may be part of the original formed crystal structure, or may be induced by the various processing, handling and treatment steps.

Various methods and apparatus for detection of such crystal defects have been used. Early methods of crystal defect detection included microscopic detection, Raman scattering, photoluminescence or x-ray topography. However, these techniques were time consuming, required expensive equipment, and typically provided information on only a very small area of the wafer. More recent developments include Scanning Infrared Depolarization (SIRD).

SUMMARY OF THE INVENTION

Silicon and GaAs are optically isotropic cubic materials. Detection of defects in such materials can be found by looking at the mechanical stress field using the photoelastic effect of such materials. That is, stress in such materials cause optical anisotrophy and the refractive index of the material becomes a tensor of the applied stress. As a result, only light with defined polarization directions collinear with two principle axes of the cut ellipse of the refractive index tensor may propagate through the crystal. These two beams, the ordinary and extraordinary beam, travel with different speeds and cause an optical bifringence effect that effectively relates to the anisotrophy or amount of stress present. The phase shift between the two beams can be determined by analyzing the depolarization of the original polarized light after penetration through the wafer using a transmission polarimeter. By scanning a wafer surface with normally incident light, one can provide a non-destructive evaluation method for imaging of wafer crystal defects.

Such a method is faster, and provides full wafer mapping capability. However, most efforts have been expended at identification of crystal defects of a particular semiconductor wafer, without much focus on the source of the defects.

Wafer supports are used to support the semiconductor wafer at various stages of wafer processing. One example of a wafer support is a susceptor, commonly used in the formation of an epitaxial layer on the wafer through epitaxial growth. During such a process, a semiconductor wafer of a certain diameter, such as 100–400 mm, is placed on a susceptor suitably shaped to support the wafer. The wafer and wafer support (susceptor) are then placed in a controlled furnace environment containing a growth atmosphere, such as hydrogen gas. During the growth process, a reaction gas containing silicon is injected into the furnace and a resultant silicon epitaxial layer becomes deposited by reduction or thermal decomposition on the surface of the wafer. The wafer is then removed and subsequently processed. These wafer supports (susceptors) can induce defects into the semiconductor wafers for various reasons. These supports may be defective as designed, constructed, or fabricated. They may also become damaged during use or maintenance, or become damaged or defective due to improper assembly.

Wafers processed using the defective or damaged wafer support can have defects such as slip or stress, leading to breaking in the wafer manufacturing process or downstream customer processes. However, often times, the defective or damaged support is not discovered until large quantities of wafers have been processed on the defective support. The resultant cost of lost product, troubleshooting and resolving of customer claims can cost hundreds of thousands of dollars.

While general techniques have been able to identify several types of crystal defects, such methods have not been fully used to identify or provide quality control analysis of crystal defects attributable to wafer support-related defects. This is because there can be many sources or causes of the defects. Basic monitoring of wafers for monitoring of quality control parameters may identify defects, but does not automatically identify those defects attributable to wafer support problems. Instead, they generally reflect a quality problem with the particular wafer itself.

There is a need for a measurement and quality control monitoring process that can readily measure processed wafers and isolate wafer support-related defects so that proper adjustment, redesign or replacement of the wafer support can occur to prevent such large outlays of cash resulting from defective wafer formation.

The inventive SIRD measurement techniques allow quick and easy characterization of depolarization stress defects across an entire wafer. One such method of SIRD measurement of wafers is performed at least twice to isolate wafer support-related defects and determine whether wafer support quality is acceptable and does not introduce stress-related defects. Support-related defects may cause a localized stress in the wafer in the vicinity of the wafer support defect. By isolating defects caused solely by wafer support defects, the identification and location of such defects on the wafer can be used to ascertain the problem wafer support defect location, allowing for quality control through either repair, adjustment, redesign or replacement of the wafer support.

An exemplary embodiment of one such method of SIRD measurement of wafers to isolate wafer support-related defects involves SIRD measurement of multiple processed wafers, each oriented differently on the wafer support. Repetitive defects on multiple wafers at same orientations relative to the wafer notch, flat, or any other alignment feature used in wafer processing, can be discounted as pre-existing or pre-processing defects. Similarly, defects on wafers processed lasermark down (inverted) that are a mirror image to defects on wafers processed lasermark up can also be discounted as pre-existing or pre-processing defects. However, defects that change location relative to the notch/flat, but correlated to the orientation relative to the wafer support/susceptor can be isolated as wafer support-related defects. Analysis of such wafer support-related defects may then be used to identify and correct the corresponding wafer support defect.

A more particular exemplary method of characterizing depolarization stress defects on semiconductor wafers using Scanning Infrared Polarization (SIRD), comprises: mounting a first semiconductor wafer on a wafer support in a first orientation; performing a processing operation on the first semiconductor wafer while being mounted on the wafer support; removing the first semiconductor wafer from the wafer support; performing a SIRD scan of the first semiconductor wafer to obtain first wafer defect information; mounting at least one second semiconductor wafer on the wafer support in a different orientation than the first orientation; performing a processing operation on the at least one second semiconductor wafer while being mounted on the wafer support; removing the at least one second semiconductor wafer from the wafer support; performing a SIRD scan of the at least one second semiconductor wafer to obtain at least one second wafer defect information; correlating the first and at least one second wafer defect information to isolate orientation dependent defects from non-orientation dependent defects; and characterizing the orientation dependent defects as wafer support-related defects.

The second, different orientation may be upside down from the first orientation.

The process may use a plurality of second semiconductor wafers, each oriented differently.

The second, different orientation may be rotationally shifted relative to the first orientation.

The second wafer need not be different from the first wafer, but may be the same as the first wafer only oriented differently from the first orientation.

Once the wafer support-related defects are characterized and isolated, the obtained positional information can be used to remedy the wafer support defect.

BRIEF DESCRIPTION OF THE DRAWINGS

The invention will be described in relation to the following drawings in which like reference numerals refer to like elements, and wherein:

FIGS. 8A–G show copies of damage depth photos of the wafer defects;

DETAILED DESCRIPTION OF PREFERRED EMBODIMENTS

Figure 1:
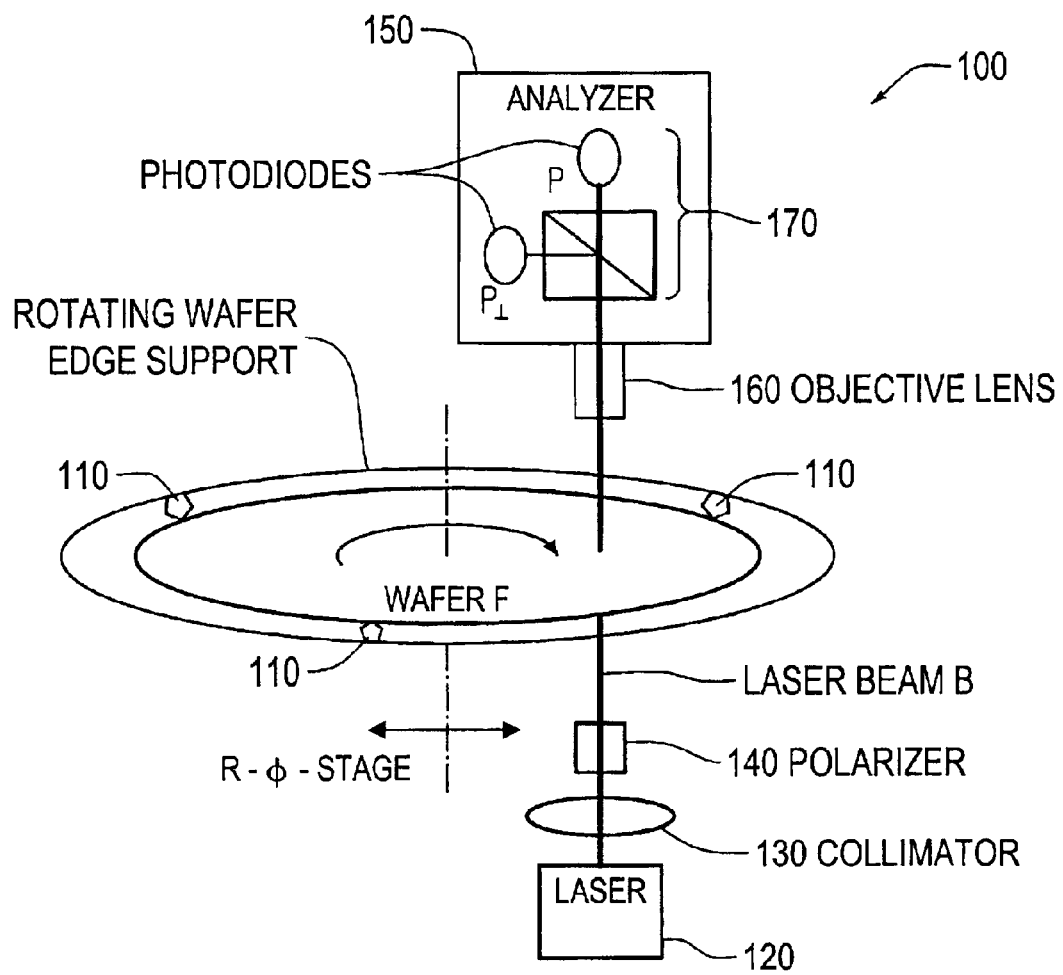
FIG. 1 shows an exemplary Scanning Infrared Depolarization tool used to perform a crystal defect characterization and isolation according to the invention.

FIG. 1 shows an exemplary Scanning Infrared Depolarization (SIRD) imager process and measurement principle used to perform aspects of the inventive methods of defect characterization. A suitable SIRD depolarization imager 100 is available from Tepla AG of Kahla, Germany or Tepla, Inc. of Carrollton, Tex. This imager is a non-contact, nondestructive analytical tool that can be used to characterize mechanical stress fields in semiconductor wafers by scanning infrared depolarization measurement. Stress fields present in the semiconductor material cause bifringence due to the photoelastic effect of the semiconductor material. The SIRD visualizes this stress by measuring and recording the depolarization of incident polarized infrared laser light transmitted through the wafer.

In particular, SIRD tool 100 includes a rotating wafer edge support 110, typically supporting three spaced edges of a semiconductor wafer F, driven by a suitable driving stage about an axis (R-$\phi$). A laser source 120 emits a laser beam B through a collimator 130 and polarizer 140 through wafer F, to an analyzer section 150, which includes an objective lens 160 leading to a detector unit 170, which includes a polarizing beam splitter and two detectors, such as photodiodes, and an unshown processor, such as a computer, PC, or RISC processor.

In use, a wafer F for inspection is placed on the driving stage and placed into rotation about axis R-$\phi$. The fixed laser beam B is scanned from the edge to the center of the wafer to complete an entire scan of the wafer area. This generates a SIRD map that can then be analyzed to characterize crystal defects through non-destructive evaluation.

Several experimental results were conducted to establish techniques useful in isolation of wafer support-related crystal defects. The results of these tests establish that it is possible to isolate wafer support-related defects and correlate these defects to a particular wafer support problem. Use of such techniques provides a fast and relatively easy method of monitoring both wafer quality and wafer support quality issues at an early stage so that such wafer support defects can be corrected before excessive wafers have been processed with unacceptable defect tolerances.

In a first experimental test, a 200 mm double side polished (P++) wafer was used. The wafer was loaded onto a wafer support. The particular type used was an ASM (Advanced Semiconductor Materials) Reactor (Epsilon 1 model-E2). This is a single wafer reactor. The susceptor was silicon coated graphite (ASM susceptor model # 16-322471D08) with the wafer notch at a 12:00 position and a prime (lasermark) side facing up. 2.8 $\mu$m of epitaxial silicon was deposited on the wafer.

Various measurements and observations on the wafer were noted to identify crystal defects. First, a KLA Tencor Surfscan SP-1 inspection system (SP-1) was used on the front side to look for lightscattering defects. Front side slip inspection was then performed using a microscope. Then, a back side halogen or other high intensity light inspection was performed. SIRD measurement was subsequently performed. Then, SP-1 inspection was performed on the back side. A scanning electron microscope was then used on the back side defects followed by optical inspection of back side defects using a microscope. Finally, optical microscope inspection was performed on the susceptor to locate defects.

Following these measurements, the back side defects were bevel polished and Wright etched for 1.5 minutes to measure the damage depth of the defects.

Figure 2:
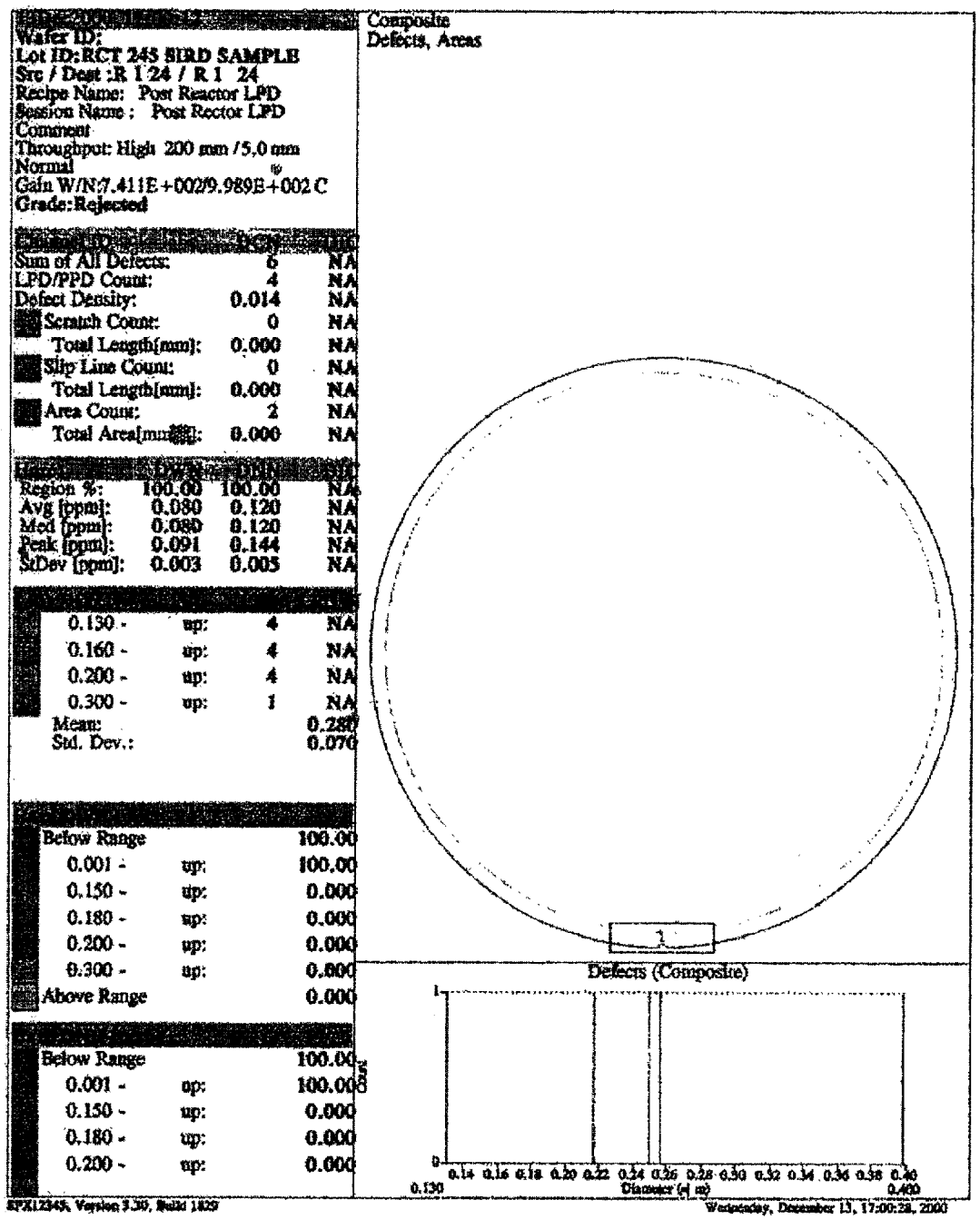
FIG. 2 is a surface scan display showing the front side of a SIRD scanned wafer after Epi deposition (post SP-1)
Figure 3:
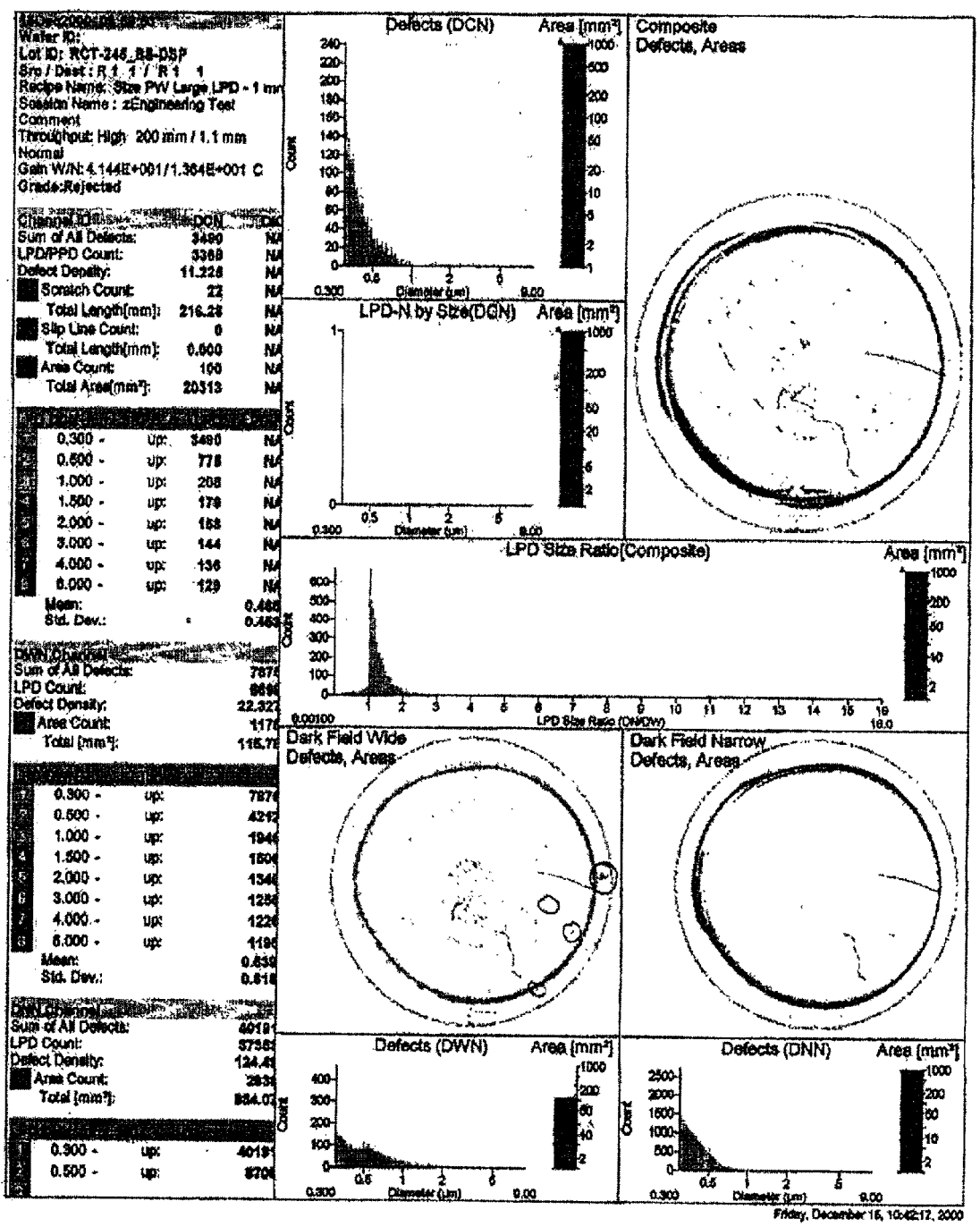
FIG. 3 shows a surface scan display showing the back side of the wafer of FIG. 2.
Figure 4:
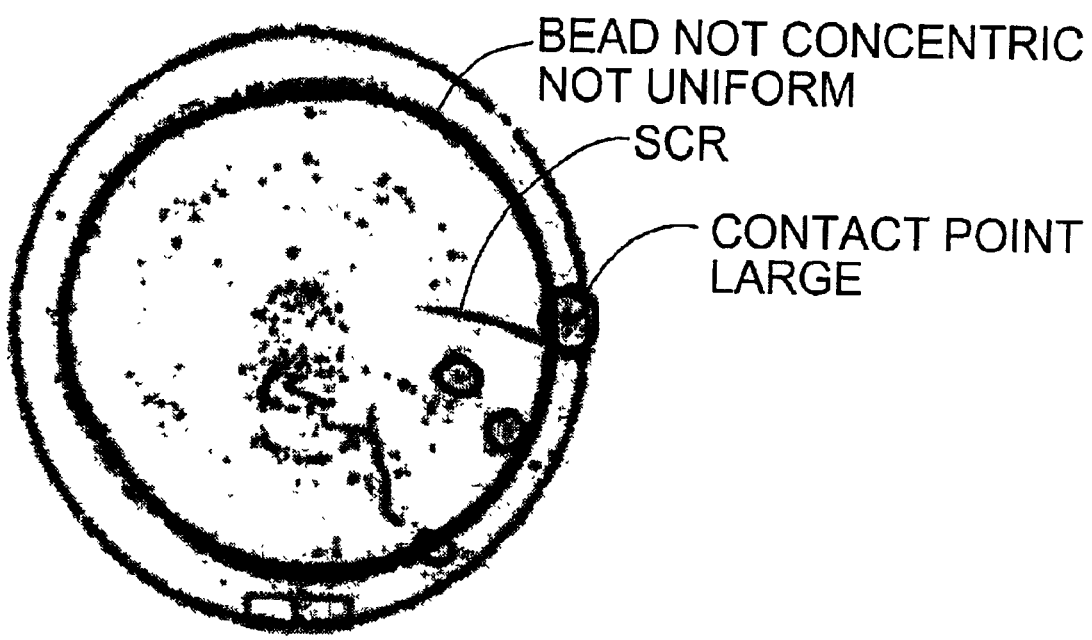
FIG. 4 shows an enlarged view of the composite area defects with circled areas indicating defects that look like LPD.

The post reactor SP-1 measurement found the following information: 4 localized light scattering defects of ≧0.13 μm, 0 scratches, 0 slip, and 2 area counts (0.000 mm$^2$). See FIG. 2, which is an output from a KLA-Tencor surface scan tool SP-1. The microscope slip inspection found no front side slip. The back side H light inspection found the typical susceptor ring visible and several particles (count <5). See FIG. 3, which also is an output from a KLA-Tencor surface scan tool SP-1. Also see FIG. 4 showing possible defects. Several high spots of heights of about 20–50 μm were identified on the susceptor that correspond to defect locations on the wafer uncovered during the subsequent SIRD. A small pinhole of about 0.5 mm diameter was located approximately 2 mm away from the high spot corresponding to defect 3. See FIGS. 6C–D.

Figure 5:
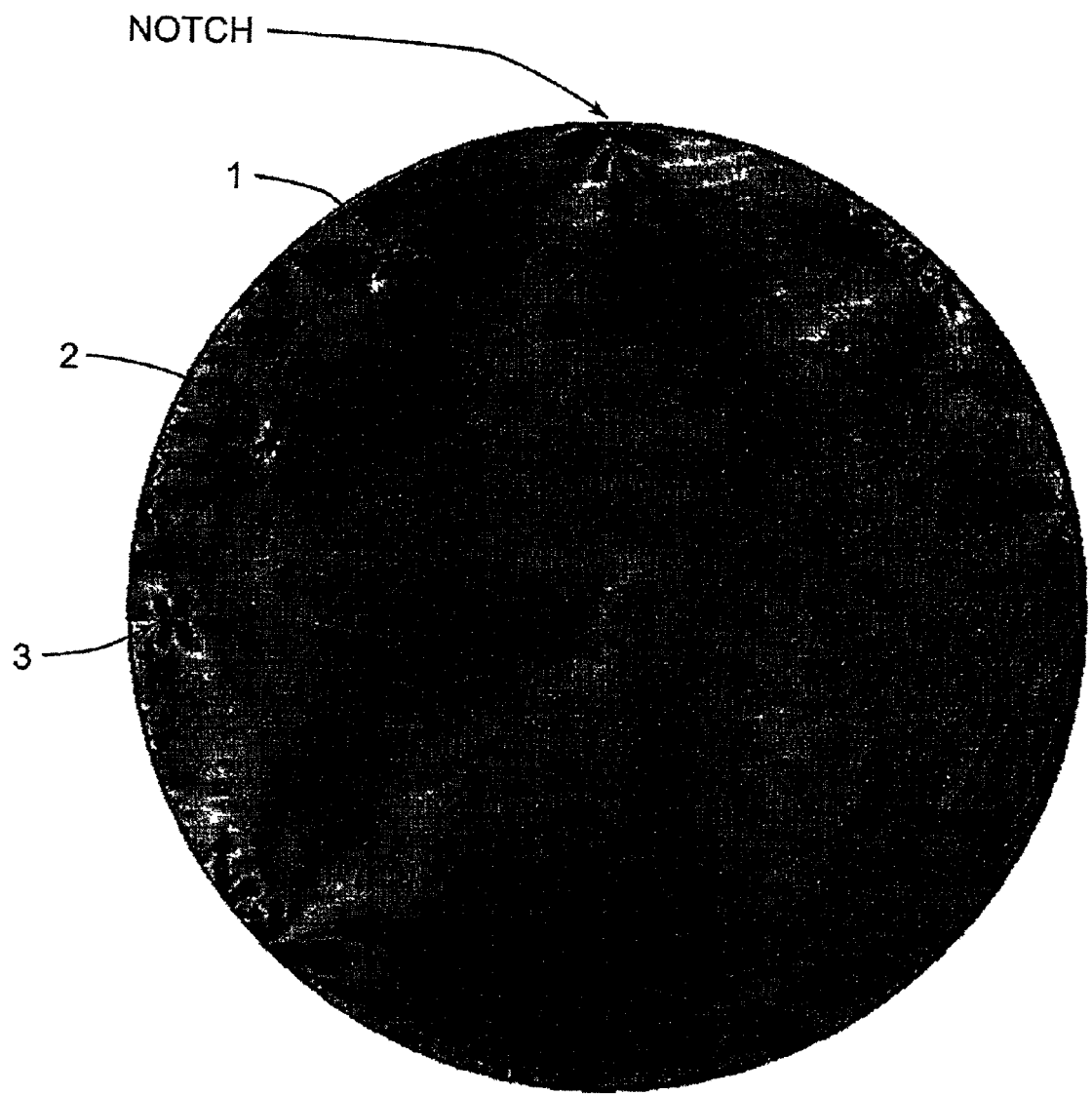
FIG. 5 shows an SIRD map of the wafer of FIG. 2 depicting depolarization stresses induced onto the wafer.

FIG. 5 shows a SIRD map generated by the SIRD tool 100, showing the wafer notch N and three identified crystal defects (defects 1–3).

Figure 6A:
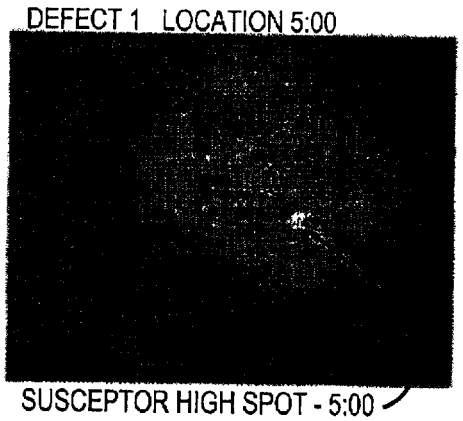
FIGS. 6A–D show copies of enlarged photographs of susceptor defects correlated to defects found on the wafer of FIG. 2.
Figure 6B:
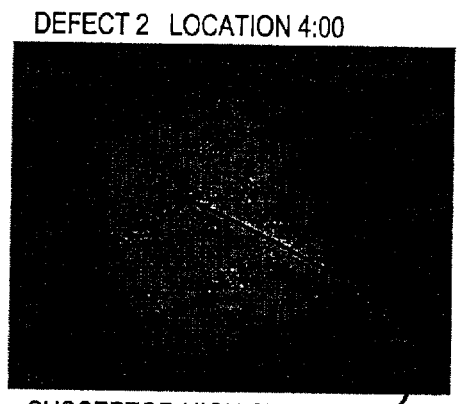
Figure 6C:
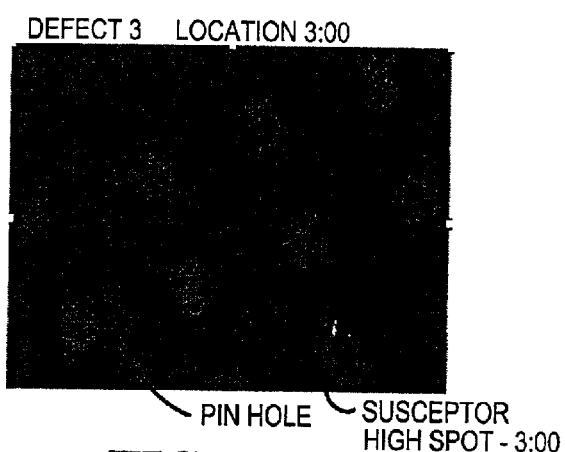
Figure 6D:
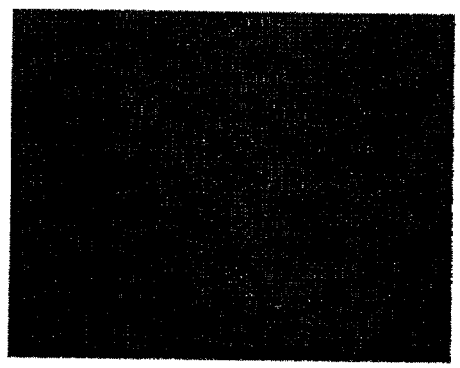
Figure 7A:
FIGS. 7A–D show copies of electron microscope photographs of wafer defects correlated to defects found on a defective susceptor.
Figure 7B:
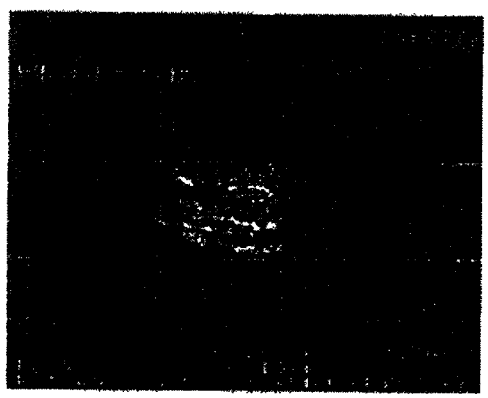
Figure 7C:
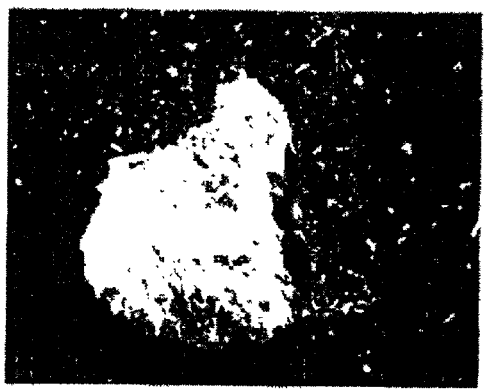
Figure 7D:

FIGS. 6A–D show magnified pictures of defects found on the test susceptor. In particular, FIG. 6A shows a susceptor high spot (defect 1). FIG. 6B shows another susceptor high spot (defect 2). FIG. 6C shows a third susceptor high spot (defect 3). FIG. 6D shows a more magnified view of the defect identified in FIG. 6C.

The wafer defects included large gouges in the wafer back side approximately 40–120 μm in size. The region surrounding the defect often exhibited slip and micro cracks. Defect 3 included a large imbedded particle. See FIGS. 7A–D showing enlarged electron microscope (SEM) photographs of the three defects (FIG. 7D being a magnification of FIG. 7C) and the embedded particle. Energy dispersive X-ray measurement indicated the presence of silicon and carbon with a lot of noise between the peaks, but no identifiable peaks for other elements. It is possible that the large particle in defect 3 is silicon carbide.

The damage depth after the bevel polish and etch steps was found to be 43 μm for defect 1 ($\Delta D_{max}$=0.978 kDU) and 32 μm for defect 2 ($\Delta D_{max}$=0.500 kDU). $\Delta D_{max}$=Max-Min polarization for the defect, which is proportional to the stress in the defect. Damage depth was not determinable for defect 3 because the sample would not bevel polish. However, since defect 3 ($\Delta D_{max}$) was much larger (about 6.78 kDu) than defects 1 and 2, it is expected that the damage depth is much greater than 40 μm. See FIGS. 8A–G, which show various defects. In particular, FIG. 8A shows defect 1. FIG. 8B shows defect 2. FIG. 8C shows defect 3. FIGS. 8D–E show the first and second defects from a side view before bevel polish. FIGS. 8F and 8G show damage depths of 42.9–43.4 μm for defect 1 and 31–31.5 μm for defect 2.

In a second test, four wafers were processed, each mounted in different orientations on the wafer support. As in the first test, 200 mm double sided polished (P++) wafers were used. Each of the wafers was loaded onto a wafer support/susceptor with the wafer at a different orientation relative to the support. See Table 1 showing the exemplary orientations used. However, the invention is not limited to these and may include other orientations. What is important is that the multiple wafers be oriented differently. As in the first test, 2.8 μm of epitaxial silicon was deposited on the ASM Reactor.

TABLE 1

| SLOT | LASERMARK SIDE FACING | NOTCH LOCATION (viewed from top of RX cassette) |
|---|---|---|
| 6 | Susceptor | 10:00 (approx. 270°) |
| 8 | Up | 6:00 (approx. 180°) |
| 10 | Susceptor | 2:00 (approx. 90°) |
| 12 | Up | 12:00 (approx. 0°) |

Various measurements and observations on each wafer were noted. First, prior to subsequent measurements, the graphite susceptor was etched to remove any deposited silicon, marked and removed. Then, SP-1 inspection was performed on the front side of each wafer. Front side slip inspection was then performed using a microscope. Then, a back side halogen light inspection was performed. SIRD measurement was subsequently performed on the back side. Then, SP-1 inspection was performed on the back side. A scanning electron microscope was then used on the front side and back side defects followed by optical microscope inspection performed on the susceptor to locate the source of repeating defects.

Interestingly, the pattern of defects detected on SIRD changed compared to the wafer measured in test 1. Many new defects were visible in the center region of the wafers compared to the wafer of test 1. It is not fully determined why these "new" defects were not present on the test 1 wafer even though susceptor high spots were correlated with positions. This phenomena could be related to susceptor degradation due to handling etc., between the two tests.

It was noted that the defects changed location relative to the notch, but were in the same location relative to the position on the susceptor, regardless of prime side orientation. If the defects were repetitive and present on the wafers prior to deposition of the Epi, the defects for the wafers processed lasermark side down should have been a mirror image of the wafers processed lasermark side up. See FIG. 8.

Figure 9B:
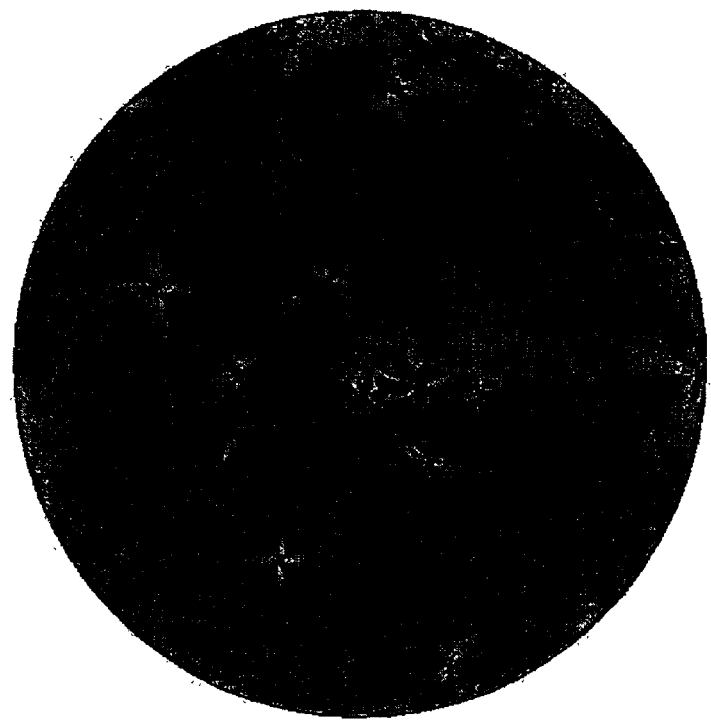
FIGS. 9A–D shows copies of SIRD maps of four scanned wafers, each scanned with a different orientation relative to the wafer support/susceptor, depicting depolarization stresses induced onto the wafers.
Figure 9A:
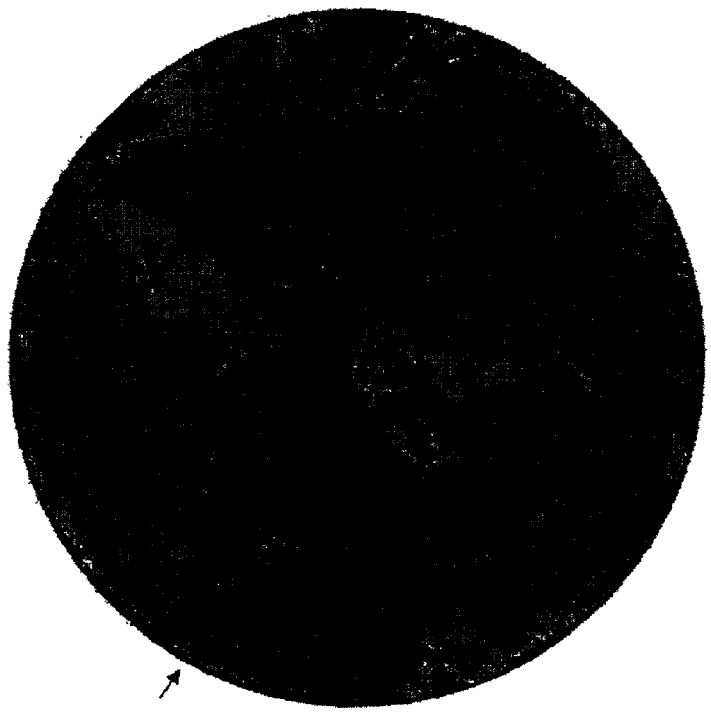
Figure 9D:
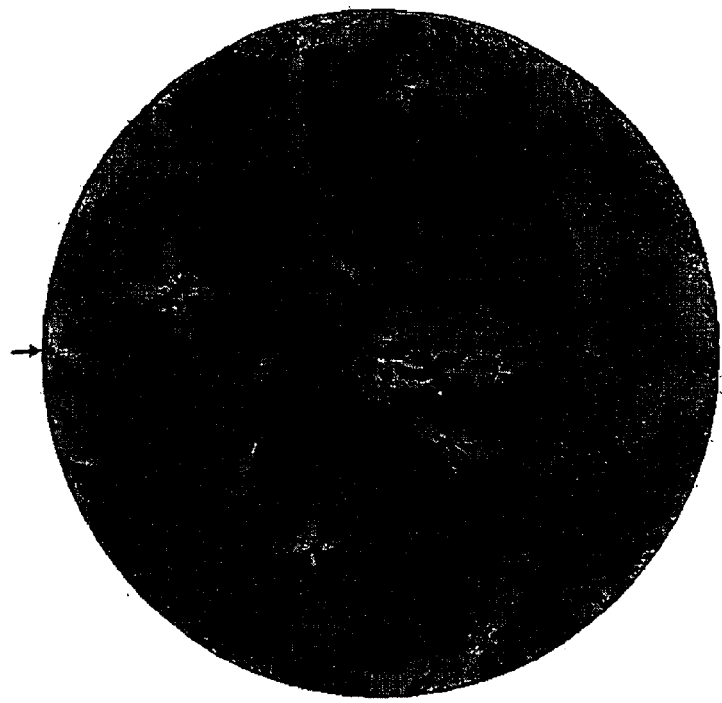
Figure 9C:
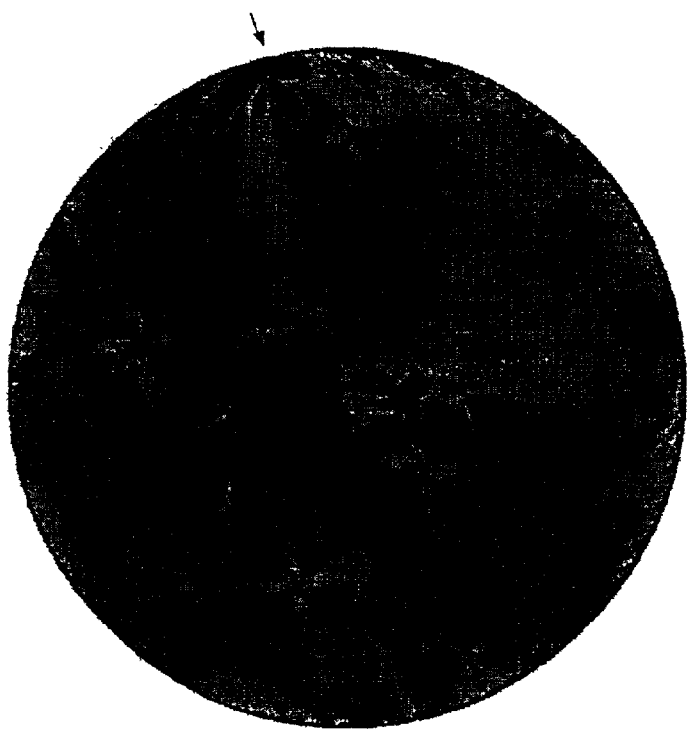

FIGS. 9A–D show SIRD maps of the stress bifringence for each of the four tested wafers. The arrow in the figures denotes the notch position on the map for each wafer. As noted in Table 1, FIG. 9A is the first wafer oriented approximately 270° relative to the notch with the lasermark side on the susceptor. Note the various labeled defects. FIG. 9B is the second wafer oriented at approx. 180° relative to the notch with the lasermark side up. FIG. 9C is the third wafer oriented at approx. 90° relative to the notch with the lasermark side on the susceptor. FIG. 9D is the fourth wafer oriented at approx. 0° relative to the notch with the lasermark side up.

The three small rectangular regions located at approximately 10:00, 2:00 and 6:00 relative to the notch can be ignored. These correspond to SIRD wafer supports (same as element 110 in FIG. 1) and were induced during the supporting of the wafers during SIRD measurement. The defect locations for wafers processed lasermark side down do not result in a mirror image compared to lasermark side up wafers. This indicates that the defects are not repetitive defects present on the wafers prior to the Epi deposition. Note that nearly all of the point defects in the central region of the wafers correlate from wafer-to-wafer when corrected for wafer orientation on the susceptor.

Test 1 correlated the SIRD detected defects to high spots on the susceptor. Test 2 further showed that many of the defects detected by SIRD were repetitive defects caused by the susceptor.

Based on these results, it was found that SIRD measurement can be valuable for qualifying susceptor design changes and routine monitoring of susceptor condition and wafer quality. Large values of $\Delta D_{max}$ correlate to increased stress and, possibly, damage depth. As such, depth could possibly be determined in a non-contact, non-destructive manner, without necessitating a bevel polish or etch to determine defect depth. Additionally, by measurement of multiple wafers in multiple orientations, defects attributable to wafer support-induced defects can be isolated from defects pre-existing in the wafer or caused by other processes. Such information is not only beneficial to ensure quality control of the wafers themselves, but can be used as cost-saving measures to monitor susceptor quality and initiate susceptor design changes.

Figure 10:
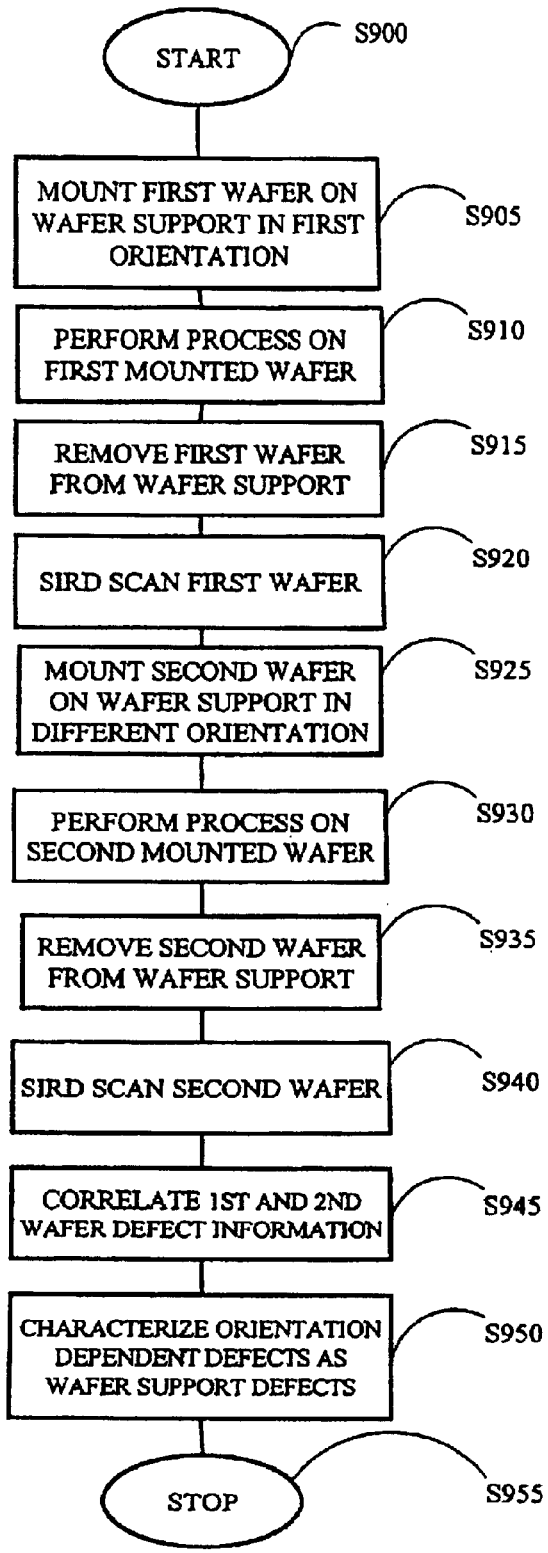
FIG. 10 shows a flow chart for SIRD measurement and isolation of wafer support-related defects according to an exemplary embodiment of the invention.

One exemplary process of isolating wafer support-related defects will be described with reference to FIG. 10. The process starts at step S900 and proceeds to step S905 where a first semiconductor wafer is mounted on a wafer support, preferably a susceptor, in a first orientation relative to the wafer support. Then, at step S910 a first wafer process is performed on the mounted wafer. For example, an epitaxial growth layer may be formed. Then, after the process is completed, the first wafer in step S915 is removed from the wafer support. At step S920, the first wafer is scanned by a SIRD tool to obtain first wafer defect information.

At step S925, a second wafer is mounted on the same wafer support, preferably a susceptor, in a second, different orientation from that used for the first wafer. Then, at step S930, a first wafer process is performed on the mounted wafer. Preferably, the process is the same as that performed on the first wafer. Again, this may be epitaxial growth. Then, after the wafer process is completed, the second wafer in step S935 is removed from the wafer support. As step S940 the second wafer is scanned by the SIRD tool to obtain second wafer defect information.

At step S945, the first and second wafer defect information is correlated to characterize and isolate semiconductor wafer defects. This can be by first orienting the data according to the wafer notch/flat (i.e., so that defect locations are commonly measured relative to the wafer notch/flat). Then, it can also be by orienting the data according to mounting positions (i.e., so that defect locations are commonly measured relative to the orientation of the wafer support). Then, at step S950, this correlated data is used to characterize wafer defects as either being wafer support related or not. Defects commonly oriented relative to the wafer notch for same-side defects are characterized as being attributable to pre-processing defects occurring prior to the process performed on the wafer support. Similarly, when the orientation difference is one wafer being mounted lasermark side up and the other lasermark side down, if the wafer defects are mirror-image of each other, this also signifies a pre-existing defect not induced by the wafer support. However, all defects whose location varied relative to the wafer notch, but were in the same location relative to the mounting position on the susceptor, are characterized as wafer support-related defects. Regardless of the type or cause of defect, the defect depth can be determined by looking at $\Delta D_{max}$, which varies with measured stress. The process stops at step S955.

Figure 11:
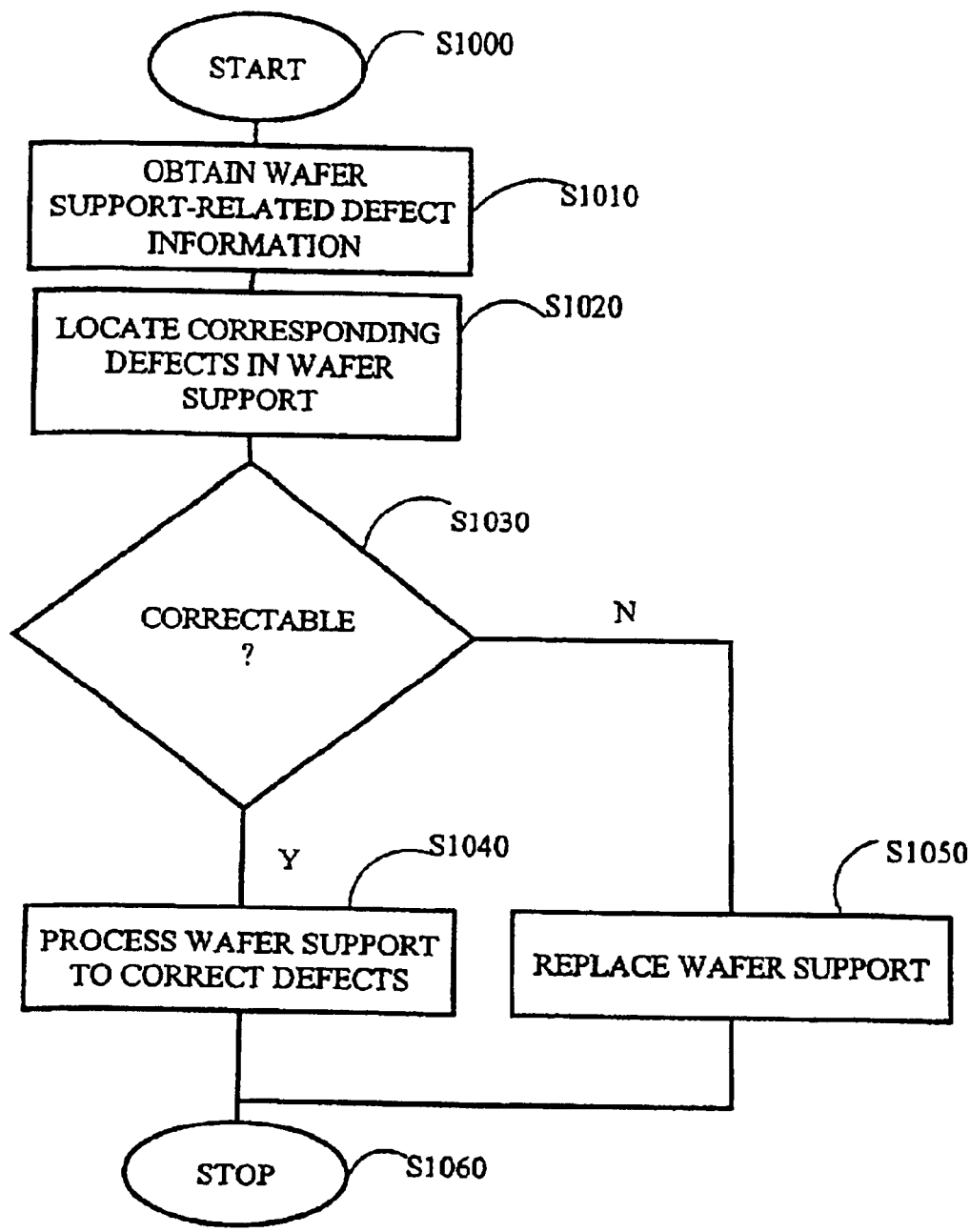
FIG. 11 shows a flow chart for wafer support correction using the information obtained from the process of FIG. 10.

FIG. 11 shows a flow chart outlining a basic process for correction of isolated and characterized wafer support-related defects. The process starts at step S1000. At step S1010 wafer support-related defect information is obtained. This may be achieved by the process of FIG. 10. Then, at step S1020 locations on the wafer support corresponding to the wafer support-related defects are obtained. At step S1030, it is determined whether the wafer support defects are correctable. This may be obtained by visual inspection, microscopic inspection or other inspection techniques. If the defects are correctable, the process advances to step S1040 where the wafer support is processed to correct the noted defects. If, however, step S1030 determines that the errors are not correctable, flow advances to step S1050 where the wafer support is replaced. The process stops at step S1060.

While this invention has been described in conjunction with the exemplary embodiment outlined above, it is evident that many alternatives, modifications and variations will be apparent to those skilled in the art. Accordingly, the exemplary embodiments of the invention, as set forth above, are intended to be illustrative, not limiting. Various changes may be made without departing from the spirit and scope of the invention.

What is claimed is:

1. A method of characterizing depolarization stress defects on semiconductor wafers using Scanning Infrared Polarization (SIRD), comprising:

mounting a first semiconductor wafer on a wafer support in a first orientation;

performing a processing operation on the first semiconductor wafer while being mounted on the wafer support;

removing the first semiconductor wafer from the wafer support;

performing a SIRD scan of the first semiconductor wafer to obtain first wafer defect information;

mounting at least one second semiconductor wafer on the wafer support in a different orientation than the first orientation;

performing a processing operation on the at least one second semiconductor wafer while being mounted on the wafer support;

removing the at least one second semiconductor wafer from the wafer support;

performing a SIRD scan of the at least one second semiconductor wafer to obtain at least one second wafer defect information;

correlating the first and at least one second wafer defect information to isolate orientation dependent defects from non-orientation dependent defects; and characterizing the orientation dependent defects as wafer support-related defects.

2. The method according to claim 1, wherein the at least one second wafer is a plurality of wafers, each oriented in a different orientation from the first wafer and others of the at least one second wafer.

3. The method according to claim 2, wherein the plurality is three, for a total of four wafers being used.

4. The method according to claim 1, wherein the defect information includes defect location, and the step of correlating includes correlating the defect location information relative to the mounting position on the wafer support.

5. The method according to claim 4, wherein the wafers each include a wafer alignment feature, and the step of correlating also includes correlating the defect location information relative to the wafer alignment feature.

6. The method according to claim 1, wherein one of the wafers is mounted lasermark side up relative to the wafer support and another of the wafers is mounted lasermark side down relative to the wafer support.

7. The method according to claim 1, wherein the at least one second wafer is mounted on the wafer support in a position rotationally shifted relative to the first orientation.

8. The method according to claim 1, wherein the at least one second wafer includes three wafers, each of which being mounted in a different orientation, with at least one of the three second wafers being mounted with a lasermark side mounted opposite that of the first wafer, and at least another of the three second wafers being mounted on the wafer support with a lasermark side mounted on the same side as that of the first wafer, but in a position rotationally shifted relative to the first orientation.

9. The method according to claim 4, wherein said step of characterizing characterizes a defect in one wafer that shares a defect location with a defect from one or more other ones of the wafers when correlated to wafer support position as a wafer support-related defect.

10. The method according to claim 5, wherein said step of characterizing considers a defect in one wafer that shares a defect location with a defect from one or more other ones of the wafers when correlated to wafer notch position as a non-wafer support-related defect.

11. The method according to claim 6, wherein the defect information includes defect location, and said step of characterizing characterizes defects in the lasermark side up wafer that are a mirror image of defects in the lasermark side down wafer as a non-wafer support-related defect.

12. The method of claim 1, further comprising a step of determining presence and quantity of defects by analyzing polarization stress amounts from the scanned defect information.

13. The method of claim 12, wherein the polarization stress amount $\Delta D_{max}$=Max−Min polarization is used to approximate depth.

14. The method of claim 1, further comprising a step of locating corresponding defects in the wafer support corresponding to the characterized wafer support-related defects.

15. The method of claim 14, further comprising a step of determining whether the wafer support may be corrected.

16. The method of claim 15, further comprising a step of either correcting or replacing the wafer support based on the step of determining.

17. The method of claim 1, wherein the at least one second wafer is the same as the first wafer, only oriented differently from the first orientation.

* * * * *